US00PP18304P2

(12) United States Plant Patent
Jepsen

(10) Patent No.: US PP18,304 P2
(45) Date of Patent: Dec. 11, 2007

(54) *KALANCHOE* PLANT NAMED 'MONA'

(50) Latin Name: *Kalanchoe blossfeldiana*
Varietal Denomination: Mona

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 11/435,973

(22) Filed: May 17, 2006

(51) Int. Cl.
*A01H 5/00* (2006.01)

(52) U.S. Cl. ..... Plt./337
(58) Field of Classification Search ..... Plt./337
See application file for complete search history.

(56) References Cited

U.S. PATENT DOCUMENTS

PP10,486 P * 7/1998 Jepsen ..... Plt./337
PP12,310 P2 * 12/2001 Jepsen ..... Plt./337

OTHER PUBLICATIONS

UPOV ROM GTITM Computer Database 2006/04 Citation for 'Mona'.*

* cited by examiner

*Primary Examiner*—Wendy C. Haas
(74) *Attorney, Agent, or Firm*—C. A. Whealy

(57) ABSTRACT

A new and distinct cultivar of *Kalanchoe* plant named 'Mona', characterized by its upright, uniform and moderately vigorous growth habit; dark green-colored leaves; uniform, freely and early flowering habit; large double red purple-colored flowers; and excellent postproduction longevity.

1 Drawing Sheet

Botanical designation: *Kalanchoe blossfeldiana.*
Cultivar Denomination : 'Mona'.

BACKGROUND OF THE INVENTION

The present invention relates to a new and distinct cultivar of *Kalanchoe,* botanically known as *Kalanchoe blossfeldiana,* and hereinafter referred to by the name 'Mona'.

The new *Kalanchoe* is a product of a planned breeding program conducted by the Inventor in Hinnerup, Denmark The objective of the breeding program is to create new freely-flowering *Kalanchoe* cultivars with attractive foliage and flower coloration.

The new *Kalanchoe* originated from a cross-pollination made by the Inventor in Hinnerup, Denmark in March, 2003, of the *Kalanchoe blossfeldiana* cultivar KJ 2001 1855, not patented, as the female, or seed, parent with the *Kalanchoe blossfeldiana* cultivar Purple Jaqueline, disclosed in U.S. Plant Pat. No. 12,310, as the male, or pollen, parent. The cultivar Mona was discovered and selected by the Inventor as a flowering plant from within the progeny of the stated cross-pollination in a controlled environment in Hinnerup, Denmark in November, 2003.

Asexual reproduction of the new *Kalanchoe* by vegetative terminal cuttings in a controlled environment in Hinnerup, Denmark since February, 2004, has shown that the unique features of this new *Kalanchoe* are stable and reproduced true to type in successive generations.

SUMMARY OF THE INVENTION

The cultivar Mona has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Mona'. These characteristics in combination distinguish 'Mona' as a new and distinct cultivar of *Kalanchoe:*

1. Upright, uniform and moderately vigorous growth habit.
2. Dark green-colored leaves.
3. Uniform, freely and early flowering habit.
4. Large double red purple-colored flowers.
5. Excellent postproduction longevity.

Plants of the new *Kalanchoe* can be compared to plants of the female parent, the cultivar KJ 2001 1855. Plants of the new *Kalanchoe* differ from plants of the cultivar KJ 2001 1855 in the following characteristics:

1. Plants of the new *Kalanchoe* are more compact than plants of the cultivar KJ 2001 1855.
2. Plants of the new *Kalanchoe* have smaller and darker green-colored leaves than plants of the cultivar KJ 2001 1855.

Plants of the new *Kalanchoe* can be compared to plants of the male parent, the cultivar Purple Jaqueline. Plants of the new *Kalanchoe* differ from plants of the cultivar Purple Jaqueline in the following characteristics:

1. Plants of the new *Kalanchoe* have longer leaves than plants of the cultivar Purple Jaqueline.
2. Plants of the new *Kalanchoe* have larger flowers than plants of the cultivar Purple Jaqueline.
3. Plants of the new *Kalanchoe* have double flowers whereas plants of the cultivar Purple Jaqueline have single flowers.

Plants of the new *Kalanchoe* can be compared to plants of the *Kalanchoe blossfeldiana* cultivar Jodie, not patented. In side-by-side comparisons conducted in Hinnerup, Denmark, plants of the new *Kalanchoe* differed from plants of the cultivar Jodie in the following characteristics:

1. Plants of the new *Kalanchoe* had slightly smaller flowers than plants of the cultivar Jodie.
2. Flowers of plants of the new *Kalanchoe* had fewer petals than flowers of than plants of the cultivar Jodie.
3. Plants of the new *Kalanchoe* flowered earlier than plants of the cultivar Jodie.
4. Plants of the new *Kalanchoe* and the cultivar Jodie differed in flower color.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.*

The photograph at the top of the sheet comprises a side perspective view of a typical flowering plant of 'Mona' grown in a container.

The photograph at the bottom of the sheet comprises a top perspective view of the a typical flowering plant of 'Mona' grown in a container.

DETAILED BOTANICAL DESCRIPTION

The photographs and following observations, measurements and values describe plants grown in Hinnerup, Denmark in a glass-covered greenhouse during the winter and under conditions which closely approximate commercial production. During the production of the plants, day temperatures were about 19° C., night temperatures were about 21° C. and light levels ranged from 10 kilolux to 50 kilolux. Unrooted cuttings were directly stuck in 10-cm containers and received long day/short night conditions (more than 14 hours of light) for about two weeks; plants then received photoinductive short day/long night conditions (minimum 14 hours darkness) until flowering. Plants were about 12 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Mona.

Parentage:

*Female, or seed, parent.*—*Kalanchoe blossfeldiana* cultivar KJ 2001 1855, not patented.

*male or pollen parent.*—*Kalanchoe blossfeldiana* cultivar Purple Jaqueline, disclosed in U.S. Plant Pat. No. 12,310.

Propagation:

*Type.*—By vegetative terminal cuttings.

*Time to initiate roots.*—About two to three weeks at temperatures of 19° C. to 21° C.

*Time to produce a rooted young plant.*—About 21 to 24 days at temperatures at 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 6-cm to 10-cm containers.

*Plant height at flowering.*—About 27 cm.

*Plant diameter at flowering.*—About 25 cm.

*Branching habit.*—Usually about four to six lateral branches develop per plant. Pinching (removal of the terminal apex) is not required but will enhance lateral branch development.

Lateral branch description:

*Length.*—About 8 cm to 11 cm.

*Diameter.*—About 5 mm.

*Internode length.*—About 1.5 cm to 2 cm.

*Aspect.*—Erect.

*Strength.*—Strong.

*Texture.*—Smooth, glabrous.

*Color.*—146A.

Foliage description:

*Arrangement.*—Opposite, simple; generally symmetrical.

*Length, vegetative plants.*—About 8 cm to 12 cm.

*Width, vegetative plants.*—About 4 cm to 7 cm.

*Length, generative plants.*—About 5 cm to 12 cm.

*Width, generative plants.*—About 2 cm to 7 cm.

*Shape.*—Ovate.

*Apex.*—Obtuse.

*Base.*—Obtuse.

*Margin.*—Crenate.

*Texture, upper and lower surfaces.*—Glabrous; leathery, succulent.

*Venation pattern.*—Pinnate.

*Color.*—Developing and fully developed foliage, upper surface: 147A; venation, 147A. Developing and fully developed foliage, lower surface: 147B; venation, 147B.

*Petiole.*—Length: About 1 cm to 3 cm. Diameter: About 5 mm to 7 mm. Texture, upper and lower surfaces: Smooth, glabrous. Color, upper surface: 147A. Color, lower surface: 147B.

Flower description:

*Flower arrangement and habit.*—Double flowers arranged singly in compound dichasial cymes that arise from leaf axils. Uniform and freely flowering habit with usually about 10 to 60 open flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long conditions (at least 14 hours of darkness).

*Time to flower.*—Early flowering habit; under short day/long night photoinductive conditions, about 71 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 9 cm to 12 cm.

*Inflorescence diameter.*—About 6 cm.

*Flower diameter.*—About 2 cm.

*Flower length* (*height*).—About 8 mm.

*Flower bud.*—Shape: Obovate. Length: About 1 cm to 1.5 cm. Diameter: About 3 mm to 6 mm. Color: N74C.

*Petals.*—Arrangement: About 20 fused at the base. Length (largest petals): About 1.8 cm. Width (largest petals): About 4 mm. Aspect: Slightly upright to eventually recurved. Shape: Ovate. Apex: Mucronate. Margin: Entire to serrate. Texture, upper and lower surfaces: Smooth, glabrous. Color: When opening, upper surface: 67A. When opening, lower surface: 73B and N74A. Fully opened, upper surface: N74A; color becoming closer to N74B with development. Fully opened, lower surface: 73B with N74A.

*Sepals.*—Appearance: Four fused at the base. Length: About 7 mm. Width: About 3 mm. Shape: Lanceolate. Apex: Acute. Margin: Entire. Texture, upper and lower surfaces: Smooth; glabrous. Color, immature, upper and lower surfaces: 144A. Color, mature, upper and lower surfaces: 144A.

*Peduncles.*—Length: About 1 mm to 6 mm. Diameter: About 1 mm. Aspect: Erect to perpendicular to vertical. Strength: Strong. Texture: Smooth, glabrous. Color: 137B.

*Reproductive organs.*—Androecium: Stamen number: About five to ten per flower. Anther shape: Elliptic, flat. Anther size: About 1 mm by 1 mm. Anther color: Close to 22B. Amount of pollen: Moderate. Pollen color: Close to 20A. Gynoecium: Pistil number: About four per flower. Pistil length: About 0.7 mm. Style length: About 0.5 mm. Style color: 145B. Stigma shape: Rounded. Stigma color: 145B. Ovary color: Close to 138A.

*Seed.*—Length: About 1 mm. Diameter: About 0.5 mm. Color: 144B.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes.*

It is claimed:

1. A new and distinct *Kalanchoe* plant named 'Mona' as illustrated and described.

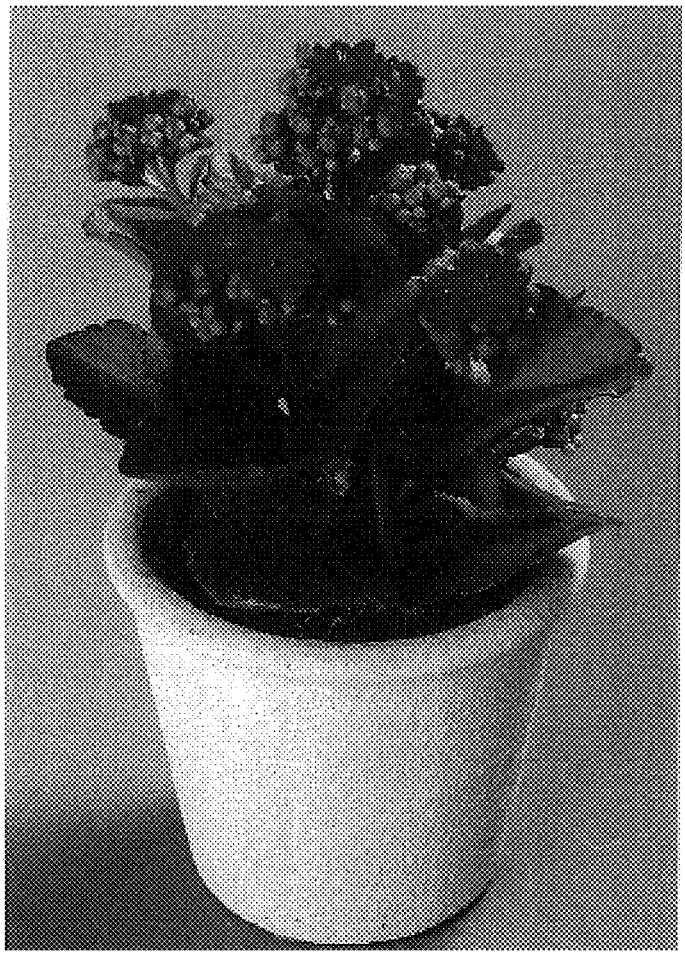
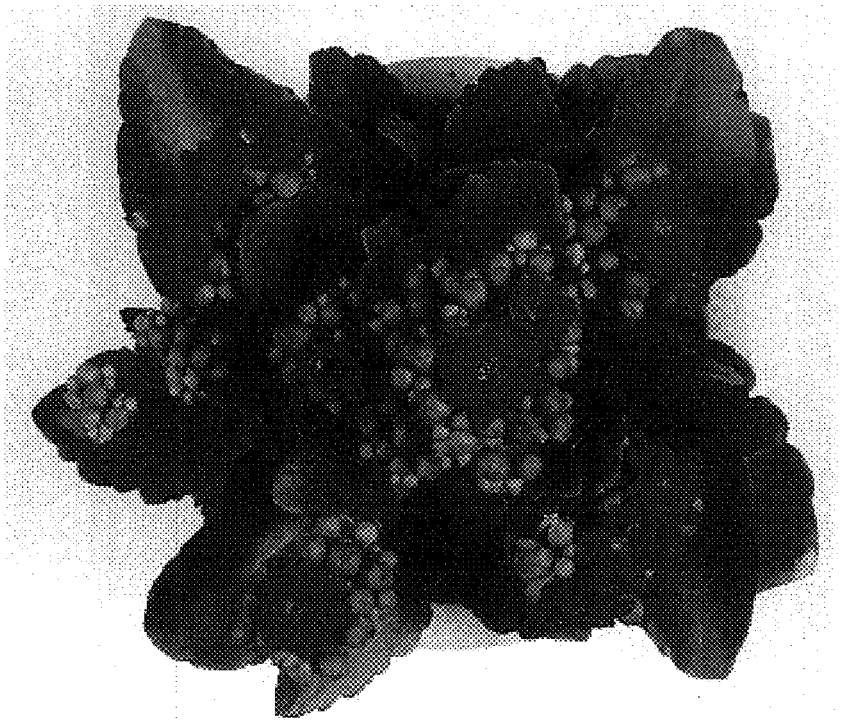

* * * * *